United States Patent [19]

Lia

[11] Patent Number: 4,794,912
[45] Date of Patent: Jan. 3, 1989

[54] BORESCOPE OR ENDOSCOPE WITH FLUID DYNAMIC MUSCLE

[75] Inventor: Raymond A. Lia, Auburn, N.Y.

[73] Assignee: Welch Allyn, Inc., Skaneateles Falls, N.Y.

[21] Appl. No.: 85,955

[22] Filed: Aug. 17, 1987

[51] Int. Cl.⁴ .............................................. A61B 1/00
[52] U.S. Cl. ............................................. 128/4; 92/92
[58] Field of Search ............................ 128/3, 4, 5, 6, 7; 254/93 R, 93 HP; 92/90, 91, 92, 247; 74/828

[56] References Cited

U.S. PATENT DOCUMENTS

| | | | |
|---|---|---|---|
| 2,844,126 | 7/1958 | Gaylord | 92/90 |
| 3,570,814 | 3/1971 | Zuppiger | 254/93 R |
| 3,610,231 | 10/1971 | Takahashi et al. | 128/6 |
| 3,669,098 | 6/1972 | Takahashi | 128/6 |
| 3,739,770 | 6/1973 | Mori | 128/6 |
| 3,799,151 | 3/1974 | Fukaumi et al. | 128/6 |
| 3,853,393 | 6/1974 | Takahashi | 128/4 |
| 4,621,618 | 11/1986 | Omagari | 128/6 |
| 4,700,693 | 10/1987 | Lia et al. | 128/4 |

Primary Examiner—William H. Grieb
Attorney, Agent, or Firm—Wall and Roehrig

[57] ABSTRACT

A fluid dynamic muscle contracts when air or hydraulic pressure is applied to it. The muscle has a long elastomeric bladder covered by a long tubular braid of flexible but inextensible fibers or filaments. When the bladder is inflated the braid is forced to expand laterally, which shortens it axially when the pressure is relieved, the muscle will relax allowing a pulling force on a tendon connected to a termination on its distal end to stretch it back to its original length. These fluid dynamic muscles can be used for bending the articulation section of a borescope or endoscope.

9 Claims, 1 Drawing Sheet

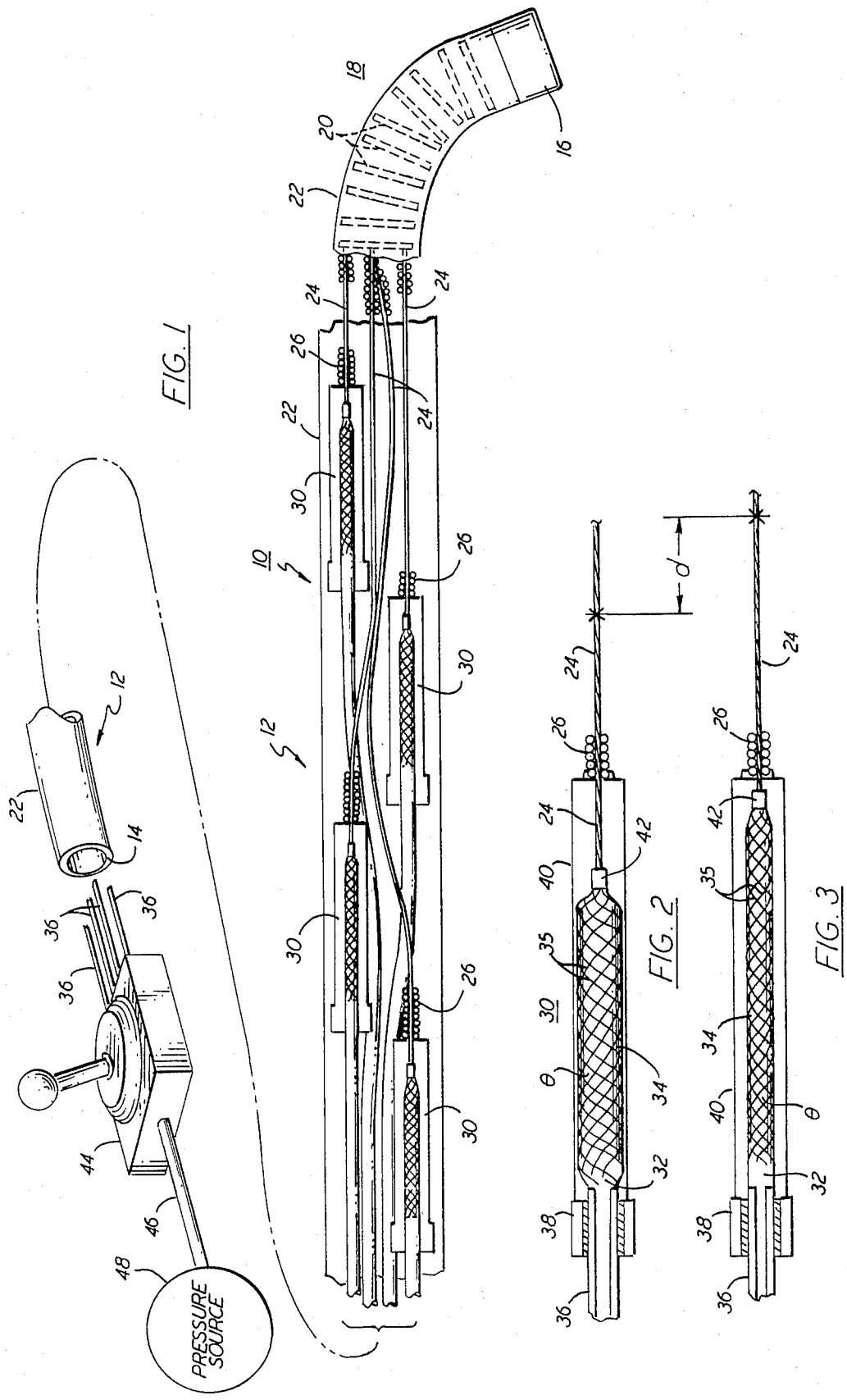

BORESCOPE OR ENDOSCOPE WITH FLUID DYNAMIC MUSCLE

BACKGROUND OF THE INVENTION

This invention relates to a fluid actuated traction motor, and is more particularly concerned with a device which contracts axially when a fluid pressure is applied to it so as to apply a tensive force, over a cable or similar tendon, to an object to be pulled.

The invention is also directed to a pneumatic or hydraulic muscle which can be incorporated within an elongated insertion tube of a borescope or like device for articulating its articulation or steering section, so that the use of extremely long steering cables can be avoided.

A borescope is generally characterized as an elongated flexible insertion tube with a viewing head at its distal or forward end, and a control housing at its proximal end for controlling or steering the forward end. Such a borescope has a bendable-tube steering section or articulation section at the distal end adjacent the viewing head. One or two pairs of control cables extend through the articulation section, and then through the remainder of the flexible insertion tube. These cables connect with a steering control in the control section. One or both pairs of these cables are differentially displaced to bend the articulation section. The viewing head can thus be remotely oriented to facilitate the inspection of an object. Borescopes are intended for visual inspection of mechanical devices such as jet engines or turbines, where it would be difficult or impossible to examine the device's internal elements directly. The borescope needs to go into narrow tortuous passageways, and must observe similar bending and steering considerations. In addition the pathway to the object can be quite long, and so it is often necessary that the borescope insertion tube be fifteen meters or more in length.

Endoscopes are similar devices, but are intended to be inserted into a body cavity, such as the colon or esophagus, for visual investigation of tissues within the cavity.

A number of types of cable actuated articulation or steering mechanisms are known, and typical ones are discussed in U.S. Pats. Nos. 3,610,231; 3,739,770; 3,583,393; 3,669,098; 3,799,151; and 4,347,837. Another steering mechanism is described in U.S. Pat. No. 4,700,693, filed Dec. 9, 1985, and having a common assignee herewith.

The articulation mechanisms for those previously-proposed endoscopes and borescopes require that the cables have a significant amount of slack or play because the articulation sections bend at discrete points rather than follow a smooth curve. However, in both the borescope and endoscope, the articulation section must be bent rather precisely in order to obtain the desired penetration without damaging delicate engine parts or injuring the patient's tissues. For these reasons cable tension must be limited and cable slack must be minimized. Where the insertion tube is long, cable slack is also included to accommodate cable tightening due to coiling and bending of the insertion tube through which the steering cables pass.

Also, when the cables are differentially displaced to effect articulation, the cable displacement is not precisely reciprocal. That is, the motion of one cable is not the exact opposite of the other. This fact results in undesirable tensioning at some times and at other times produces unwanted cable slack, which can lead to imprecise steering. Coiling of the insertion tube can produce high tension in both cables of a cable pair, which can lead to increased friction and damaging high forces on the cables and on the articulation section. If no measures are taken to compensate for this, early failure can follow.

Ideally, the steering cables should be kept short to avoid the above problems. To do this, the cables would have to terminate within the insertion tube near the articulation section, and some mechanism to draw the cables would be incorporated within the sheath of the insertion tube. Unfortunately, no known existing mechanism has been proposed for this task.

In the field of pneumatic or hydraulic devices, a fluid traction cylinder has been proposed in U.S. Pat. No. 3,570,814, for the purpose of producing a contraction or shrinking of various enclosures. There a cylinder with axial folds is wound with straps. The diameter of the cylinder increases as air pressure is applied, which tensions the straps. The device cannot be made to contract axially.

OBJECTS AND SUMMARY OF THE INVENTION

It is an object of this invention to produce a device that behaves like muscle tissue, i.e., that contracts when actuated, and thus can be suitably employed in an endoscope or borescope to avoid the drawbacks of the prior art.

It is another object of this invention to provide a mechanism which avoids the need for long steering cables that extend through the entire length of a borescope or endoscope insertion tube.

It is a further object of this invention to provide a mechanism which permits steering or articulation of a device, such as an endoscope or borescope, by means of relatively low pressure air or hydraulic fluid.

According to an aspect of this invention, a fluid dynamic muscle contracts when a fluid pressure is applied to it, thus pulling against an object, which, for example, can be a steering cable of a borescope or endoscope. The fluid dynamic muscle relaxes, and stretches when the pressure is relieved from it. The muscle is made up of an elongated balloon or bladder and a tubular braid disposed over the bladder. A conduit provides fluid pressure to the bladder. The braid is formed of a plurality of flexible, yet inextensible filaments, and is stretched between its proximal and distal ends. A tendon is affixed to a termination of the distal end and an anchor holds the proximal end of the braid. The braid filaments are wound in opposite helical spirals so as to cross at a braid angle, measured from the axis, $\theta$ that varies from a low minimum angle to a maximum of about 45° as the bladder is inflated. The tubular braid permits the bladder inside it to expand laterally when the fluid pressure is applied, but restrains the bladder such that as the bladder and tubular braid increase in diameter, the braid contracts axially. This places tension on the cable or tendon and draws it proximally.

To actuate the steering or articulation section of a borescope, there are four of these fluid dynamic muscles situated near the distal end of the insertion tube, but staggered. Each is connected to one cable of the two pairs of steering cables. Fluid conduits extend to the muscle bladders from the proximal end of the borescope insertion tube and are connected to a source of fluid pressure by means of a manual controller. In a preferred embodiment, the controller is joystick actuated.

The above and other objects, features and advantages of this invention will become apparent from the ensuing description of a preferred embodiment, which is to be considered in connection with the accompanying drawing.

BRIEF DESCRIPTION OF THE DRAWING

FIG. 1 is a schematic sectional view showing a borescope that incorporates the fluid dynamic muscle according to a preferred embodiment of the invention.

FIGS. 2 and 3 are detail sectional views the fluid dynamic muscle of this invention in a contracted and in an extended condition, respectively.

DETAILED DESCRIPTION OF A PREFERRED EMBODIMENT

With reference to the drawing, FIG. 1 schematically illustrates a borescope 10, in which an elongated flexible insertion tube 12 has a proximal end 14 and a video imager head 16 disposed at its distal end. Adjacent the head 16 is a steering or articulation section 18. This section 18 is formed of a number of spaced rings or disks 20, and is covered with a flexible sheath 22. This sheath 22 extends back over the insertion tube 12. There are two pairs of steering cables 24, with one pair arranged for bending the articulation section 18 in a vertical plane (here represented by the plane of the drawing), and the other pair of cables 24 bending the section 18 in the plane perpendicular to it, that is, in and out of the drawing. Each cable 24 has a flexible cable sheath 26 which carries the compressive reaction force corresponding to the tensive force on the associated cable 24.

In order to apply reciprocal displacing forces onto the two pairs of cables, the borescope 10 includes four pneumatic muscles 30, which are arranged in staggered fashion within the insertion tube 12 and relatively close to the steering section 18. The proximal end of each of the first, second, and third of these muscles 30 is positioned distally of the distal end of the next muscle 30. These muscles 30 are shown in greater detail in FIGS. 2 and 3.

Each pneumatic muscle 30 has an elongated bladder or balloon 32 that is formed of a flexible elastomeric closed tube. The bladder 32 is covered with a tubular braid 34 which is formed of a number of fibers or filaments 35 wound helically around the bladder 32 to cross at a braid angle $\theta$. A conduit or tube 36 extends from the proximal end of the bladder 32 through the insertion tube 12 and out the proximal end 14 thereof. An anchor termination 38 seals the proximal ends of the bladder 32 and braid 34 to the distal end of the conduit 36. A semi-rigid sheath 40 formed of a tube of synthetic resin extends distally from the anchor termination 38 and has a closed end which abuts the proximal end of the respective cable sheath 26. A forward or distal termination 42 closes the distal end of the braid 34 and connects the same to an associated one of the steering cables 24.

At the proximal end 14 of the insertion tube 12, a joystick-type controller 44 has a pressure input connected via a feed line 46 to a source of pressure 48, and has controlled pressure outlets connected to respective ones of the conduits 36.

When pressure is applied through the conduit 36 to the bladder 32, the bladder inflates and forces itself out laterally against the braid 34. The braid then is forced to expand in diameter. This reduces the length of the braid 34, and applies a pulling or tensive force on the associated cable 24. Expansion continues up until the braid 34 reaches the same diameter as the inside of the sheath 40, or until the axial shortening of the braid 34 is balanced by the pulling force on the cable 24. When the pressure is relieved from the conduit 36 and the associated bladder 32, the muscle 30 relaxes, and the tensive force on the cable 24 stretches the bladder 32 and braid 34 distally, as shown in FIG. 3. With this muscle 30, the cable 24 has a travel d as shown in FIGS. 2 and 3.

In a practical borescope or endoscope, the pneumatic muscles 30 are rather long and narrow affairs, being about 0.170 inches in diameter and about 15 inches in length. A pneumatic pressure of about 90 psi is applied from the pressure source 48, and the cable travel d is on the order of 0.5 inches. With the system as described here, a maximum tensive force of about 4 lbs. is achieved. This is sufficient for articulating or steering the section 18, but will not provide enough force that the borescope head might damage itself or any delicate parts that it is to inspect.

To maximize the elongation of the relaxed muscles, a vacuum can additionally be applied to the controller 44 for relieving pressure in one muscle 30 of an opposed pair, while pressure is applied to the other muscle 30 thereof.

The pneumatic muscles 30 as here described are relatively flexible, and can bend with the insertion tube 12 to follow tortuous paths through jet engines, turbines or other machinery.

The contraction force generated by the pneumatic muscle 30 is related to the braid angle $\theta$. As the angle $\theta$ gets larger, the contraction force reduces, but the degree of axial contraction becomes larger. When this angle $\theta$ is about 45 degrees, the contraction force F becomes very small. Consequently, the braid angle is selected so that when the braid is fully extended, as in FIG. 3, the angle $\theta$ is very small. When the braid 34 is expanded, as shown in FIG. 2, the angle $\theta$ increases up to about 45 degrees if it is not diametrically limited.

In addition to its use as a muscle for articulating a borescope, the device of this invention can also be employed for moving the needle of a pressure gauge to indicate the pressure to which the conduit 36 thereof is connected or to actuate robotic type devices.

While the invention has been described in detail with reference to a preferred embodiment, it should be understood that the invention is not limited to that precise embodiment, and that many modifications and variations thereof would present themselves to those skilled in the art without departing from the scope and spirit of this invention, as defined in the appended claims.

What is claimed is:

1. A fluid dynamic muscle which contracts when a fluid pressure is applied thereto for pulling against an object, and which relaxes when the pressure is relieved from it; comprising:
   an elongated elastomeric bladder;
   conduit means supplying said fluid pressure to said bladder;
   a tubular braid with proximal and distal ends and disposed over said bladder and formed of a plurality of flexible yet substantially inextensible filaments, the tubular braid permitting said bladder therewithin to expand laterally when said fluid pressure is applied thereto, but restraining the bladder such that as said tubular braid increases in diameter the braid contracts axially;

a semi-rigid tubular sheath over said braid and bladder;

anchor means for anchoring the proximal end of said braid to a proximal end of the sheath;

a termination closing the distal end of said tubular braid;

tendon means connected to said termination for carrying a tensive force from said braid to pull said object when said fluid pressure causes said bladder and said braid to expand; and an incompressible cable sheath over said tendon means and extending between said object and a distal end of said tubular sheath for carrying compressive reaction forces to the said semi-rigid tubular sheath.

2. Fluid dynamic muscle according to claim 1, in which said braid filaments are helically wound so as to cross at a braid angle $\theta$ which is a maximum of substantially 45 degrees when said muscle is contracted, and small when the muscle is extended.

3. A borescope or endoscope that comprises a flexible elongated insertion tube, an articulation section at a distal end of said insertion tube and having at least a first pair of steering cables for bending the articulation section in one place; at least one pair of fluid dynamic muscles each associated with a respective one of said steering cables; each said muscle including an elongated elastomeric bladder, a fluid conduit extending from the proximal end of the associated bladder to the proximal end of the insertion tube for supplying a fluid pressure to the bladder, a tubular braid with proximal and distal ends, disposed over said bladder and formed of a plurality of flexible inextensible filaments, the tubular braid permitting said bladder therewithin to expand laterally when said fluid pressure is applied to it but restraining the bladder such that as said tubular braid increases in diameter it contracts axially, anchor means for anchoring the proximal end of each said braid to a ground within said insertion tube;

a termination closing the distal end of the associated braid and connecting it to an associated one of the steering cables for applying a tensive force thereto for bending said articulation section when said fluid pressure causes said bladder and braid to expand laterally, a source of fluid pressure; and a controller for selectively applying said fluid pressure from said source to one or the other of the fluid conduits of the muscles associated with each pair of steering cables, for actuating the associated fluid dynamic muscles in such fashion as to bend said articulation section a desired degree;

wherein said fluid dynamic muscles are situated within the insertion tube near the distal end thereof to minimize play in the associated steering cables.

4. The borescope or endoscope of claim 3 wherein said controller includes a joystick having a single handle that is actuable in left-right and back-forth directions, and four controller fluid outputs that are connected respectively to said fluid conduits.

5. The borescope or endoscope of claim 3 wherein each said muscle further includes a semi-rigid tubular sheath disposed over said braid and bladder.

6. The borescope or endoscope of claim 5 wherein said anchor means includes an incompressible cable sheath over the associated steering cable and extending between said articulation section and a distal end of the associated tubular sheath, with the proximal end of said tubular sheath being affixed to the proximal end of said tubular braid.

7. The borescope or endoscope of claim 3 wherein said braid filaments are helically wound so as to cross at an angle $\theta$ which increases to no more than substantially 45 degrees when said muscle is contracted, and decreases to a substantially smaller angle when the muscle is extended.

8. The borescope or endoscope of claim 3 wherein said fluid dynamic muscles are positioned at staggered locations within said insertion tube so that the proximal end of one thereof is positioned distally of the distal end of the next.

9. The borescope or endoscope of claim 3 wherein said source of fluid pressure further includes a vacuum source, and said controller includes means for applying vacuum from said vacuum source to relieve pressure in one muscle of an opposed pair, while pressure is being applied to the other muscle thereof.

* * * * *